United States Patent [19]

Hanson et al.

[11] 4,108,602

[45] Aug. 22, 1978

[54] SAMPLE CHANGING CHEMICAL ANALYSIS METHOD AND APPARATUS

[75] Inventors: William A. Hanson, Westlake Village; Graham S. S. Barr, Canoga Park, both of Calif.

[73] Assignee: Hanson Research Corporation, Northridge, Calif.

[21] Appl. No.: 734,089

[22] Filed: Oct. 20, 1976

[51] Int. Cl.² .......................... G01N 1/14; G01N 1/18
[52] U.S. Cl. .............................. 23/230 R; 23/253 R; 23/259; 73/425.6
[58] Field of Search .................. 23/230 R, 253 R, 259; 73/425.6; 356/181, 246

[56] References Cited

U.S. PATENT DOCUMENTS

| | | | |
|---|---|---|---|
| 3,419,358 | 12/1968 | Smythe et al. | 23/253 X |
| 3,424,557 | 1/1969 | Skeggs | 23/253 R |
| 3,583,232 | 6/1971 | Isreeli | 23/259 UX |
| 3,598,532 | 8/1971 | Adams et al. | 23/253 X |
| 3,607,092 | 9/1971 | Neff | 23/259 |
| 3,708,265 | 1/1973 | Lyshkow | 23/253 X |
| 3,764,268 | 10/1973 | Kosowsky et al. | 23/259 X |
| 3,846,075 | 11/1974 | Cioffi | 23/253 X |
| 3,953,136 | 4/1976 | Hach | 23/253 X |
| 3,990,853 | 11/1976 | Godin | 23/259 |
| 3,991,055 | 11/1976 | Godin et al. | 23/259 |

Primary Examiner—R.E. Serwin
Attorney, Agent, or Firm—Albert L. Gabriel

[57] ABSTRACT

An automated sample changing chemical analysis system for sequentially analyzing a series of samples such as pharmaceutical chemical samples, the system being particularly useful for dissolution rate testing. A pressure/vacuum source provides motivation for withdrawing each sample from its respective source in sequence through a sample selector valve and transporting the sample to the flow cell of a chemical analyzer such as an U.V. Spectrophotometer, and then returning all or part of the sample to its source through the same selector valve and purging the flow cell and conduits back to the sample source. In one form each sample is simply drawn by vacuum from its source through the selector valve into the flow cell and then the entire sample is returned after analysis, by air pressure, back through the selector valve to the source, while in another form a diluent or reagent is mixed with the sample in an intermediate step to bring the sample within the testing range of the analyzer. Novel microporous filter stop means is employed to protect the pressure/vacuum source from system liquids, to accurately measure a quantity of diluent or reagent to be mixed with the sample, and to minimize bubbles in the system.

68 Claims, 8 Drawing Figures

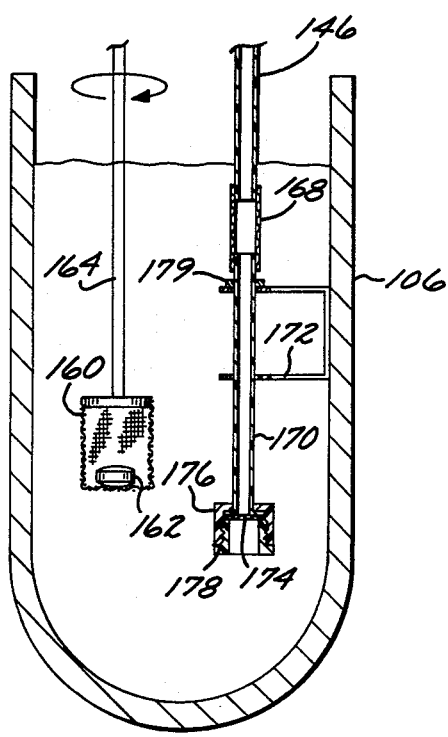
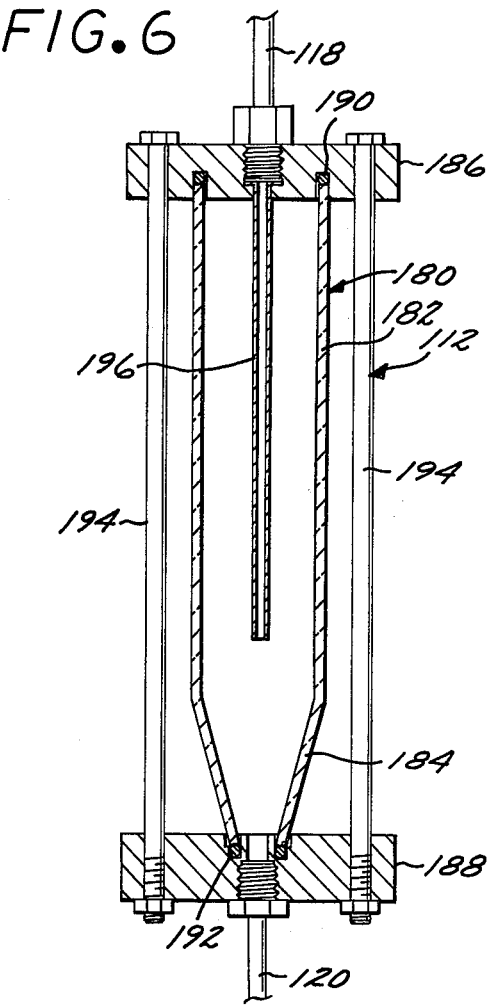
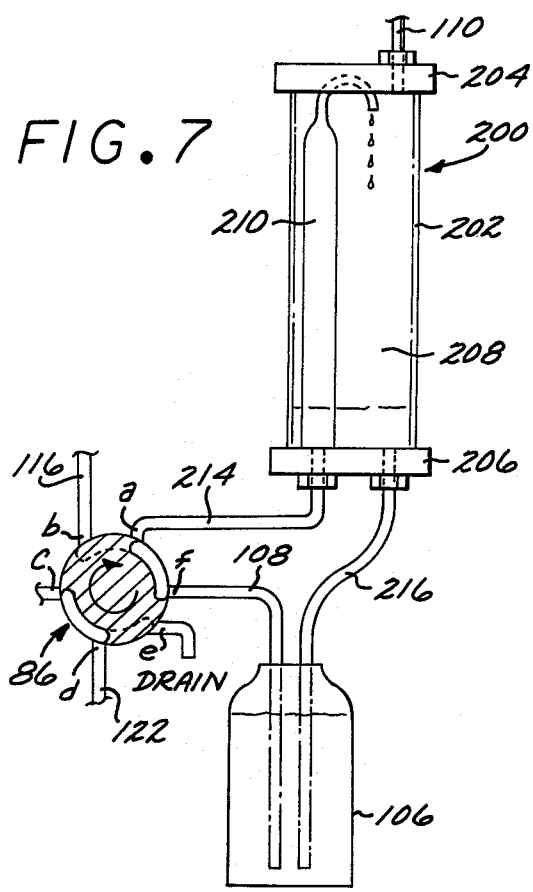
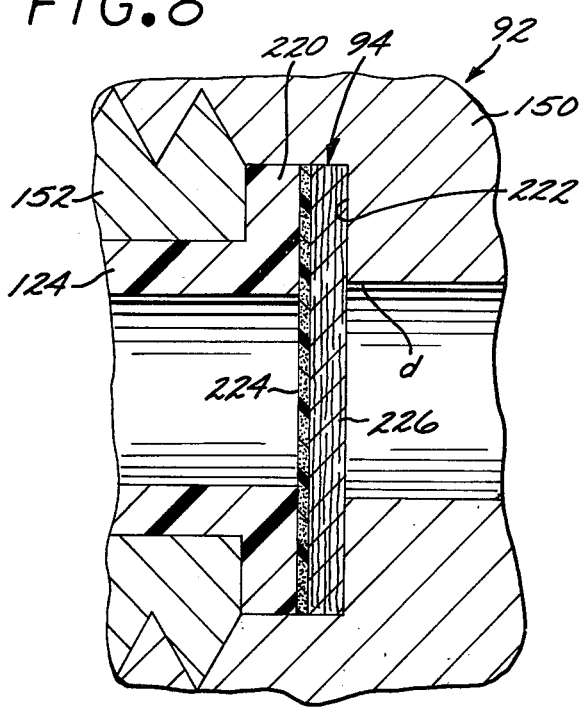

SAMPLE CHANGING CHEMICAL ANALYSIS METHOD AND APPARATUS

BACKGROUND OF THE INVENTION

1. Field of the Invention

The present invention is in the field of automated analytical chemistry systems, and is particularly directed toward automated systems for sequentially determining the dissolution rates of a series of chemical samples.

2. Description of the Prior Art

U.S. Pat. No. 3,802,272 issued Apr. 9, 1974 to Bischoff et al for Automatic Dissolution Rate Determinator illustrates and describes the state of the art prior to the present invention. Said U.S. Pat. No. 3,802,272 discloses apparatus for automatically sequentially withdrawing samples from a series of six dissolution test chambers and pumping them through the flow cell of a detector such as an ultraviolet spectrophotometer, and returning each sample to its respective dissolution chamber. A six-way intake valve and six associated intake tubes are employed for sequentially delivering the six samples to the testing apparatus, and a separate six-way return valve and six associated return tubes are employed for sequentially returning the samples to the respective sample chambers. A peristaltic pump is required for moving the samples through the apparatus, and air pressure from a separate source is employed to purge or back-flush some of the lines through the six-way intake valve after each sample has been tested to reduce carryover or crossover with the next sample to be tested.

There are several serious problems that are inherent in such prior art apparatus which are overcome by the present invention. One such problem is that the need for two separate six-way valves and associated delivery tubes makes the apparatus undesirably complicated and expensive.

Another problem with such prior art apparatus is the requirement that a peristaltic pump be employed for flowing the samples. Peristaltic pumps have long been used in the art but have the disadvantage that the working life of the active tubing in a peristaltic pump is limited to a short period, measured in hours, and the tubing must be constantly changed. This is not only a source of annoyance and trouble to the operator, but it also makes it impossible to run extended uninterrupted dissolution tests with the automated equipment over dissolution periods that are required to have a duration longer than the life of the pump tubing. This short operational life of the peristaltic pump tubing is a critical problem with respect to some delayed release drug dissolution testing wherein the testing must be conducted over periods of several days up to several weeks, it being impossible to maintain a peristaltic pump in operation without changing the tubing for such extended periods of time. A still further problem with the use of a peristaltic pump is that tetrafluorinated hydrocarbon materials which are substantially inert to most all chemicals have not been found suitable for use in peristaltic pump tubing, and the only tubing materials available for such pumps have been plastic compositions which exhibit substantial deterioration with some dissolution media and chemicals and can be a source of interfering molecules in the detection system.

A further serious problem in connection with such prior art automatic dissolution rate testing apparatus is that in some instances the concentration of chemical in the sample might be either too strong or too weak to fall within the optimum or effective range of the detector for quantitative determination of the absorbence in a spectrophotometer, fluorescence in a fluorometer, or other type of detection. In the prior art this has required replacement of flow cells attempting to come within the detector range, or separate sample processing outside of the automated system, neither of which is a satisfactory solution to the problem.

A still further problem in connection with such prior art apparatus is that the use of a separate return valve and associated tubes makes it difficult to adequately purge the lines after each sample has been tested, and usually there will be some residual sample remaining in one or more of the lines which will result in some carryover or crossover with the next succeeding test.

A still further problem in connection with such prior art automated dissolution rate testing apparatus is that the air pressure purging part of the system tends to cause bubbling or foaming in the samples, which tends to result in inaccurate readings in the detector. This problem can be a very serious one where a high degree of accuracy is required in the result.

SUMMARY OF THE INVENTION

It is therefore an object of the present invention to provide an automated sample changing chemical analysis system which is simplified in construction and wherein the required number of complex multiple-position selector valves and associated tubes is minimized.

Another object of the invention is to provide a simplified sample changing chemical analysis method and apparatus particularly adapted for sample dissolution rate testing, as for example the testing of pharmaceutical chemical samples.

Another object of the present invention is to provide automated multiple sample chemical testing method and apparatus which embodies a novel bidirectional flow of sample solutions wherein the sample solutions are withdrawn from respective sample chambers, tested and then returned to their respective sample chambers through the same sample access conduits and valve means, without employing separate sample return conduits and valve means, whereby both the method and the apparatus may be materially simplified, and liquid purging of conduits, valve means and sample filters is accomplished during return of the sample to their respective chambers.

A further object of the present invention is to provide novel automated multiple sample chemical testing method and apparatus of the character described wherein air pressure purging is employed, and novel apparatus and method steps are employed in connection with such air pressure purging to minimize interference with sample detection from the presence of bubbles or foam which tend to be generated during any such air pressure purging.

A still further object of the present invention is to provide a novel automated multiple sample chemical testing system which eliminates the requirement for a peristaltic pump, thereby enabling samples to be tested for longer periods of time, permitting more inert materials to be employed in the apparatus, and reducing part replacement problems.

A still further object of the present invention is to provide an automated multiple sample chemical testing system wherein a sample that is either too strong or too weak to come within the optimum testing range of the detector may be automatically mixed during the normal operational sequence of the system with an accurately proportioned quantity of diluent or reagent so as to bring the sample within the optimum range of the detector.

Yet a further object of the present invention is to provide an automated multiple sample chemical testing system which embodies novel filter stop method and apparatus for minimizing bubbles in the system, for protecting the air pressure source in the system, and for accurate measurement of diluent or reagent to be mixed with sample solutions.

In a simplified form of the present invention a series of sample chambers, as for example six test sample chambers and one reference sample chamber, are connected through a single sample selector step valve and sample delivery conduit to the flow cell of a sample concentration detector and overflow conduit leading from the flow cell to a pressure/vacuum source. At each selected position of the sample selector valve, vacuum from the pressure/vacuum source causes the respective sample solution to be withdrawn from its sample chamber through the selector valve and sample delivery conduit to fill the flow cell and overflow some of the solution into the overflow conduit so as to move any bubbles which may form past the flow cell and into the overflow conduit. The concentration of the sample in the flow cell is then read and recorded, and air or other gas pressure from the pressure/vacuum source then reverses the direction of flow of the sample and moves the sample back out of the overflow conduit, flow cell, sample delivery conduit and selector valve, returning the sample solution to its respective sample chamber and at the same time liquid-purging the filter associated with that sample chamber. Air or other gas from the pressure/vacuum source then follows the sample through this flow path to substantially completely purge the flow path of any of the sample solution that was just tested to minimize carryover with the next sample to be tested. The sample selector valve then shifts to the next sample, and the sequence is repeated, the selector valve preferably shifting before the pressure/vacuum source is shifted back to its vacuum mode so that a shot of air pressure will be applied to clear the new sample filter before the new sample is withdrawn from its chamber for testing.

Novel filter stop means may be employed in the overflow conduit proximate the pressure/vacuum source to protect the source against induction of any of the liquid sample solution during the vacuum-fill phase of each operational sequence.

This simplified system of the invention is modified in another form of the invention to include a source of diluent or reagent, valve and measuring conduit means, and mixing means, for measuring discrete quantities of the sample solution and either the diluent or reagent, and then mixing these measured quantities which are then passed to the flow cell and measured by the detector. This modified system employs essentially the same operational sequence as the aforesaid simplified system, but utilizes successive vacuum and pressure applications for measuring and mixing one sample during the same operational sequence of the apparatus in which a preceding mixed sample is being detected in the flow cell. The novel filter stop means of the present invention is employed with particular utility in this modified system for the accurate measurement of a measurement quantity of diluent or reagent, as well as to protect the pressure/vacuum source and to minimize bubbling in the system.

In a further modification of the system, additional valving is provided to selectively shift the system between the simplified mode of operation wherein actual sample concentration is detected, and the modified mode of operation wherein a mixture of sample solution and diluent or sample solution and reagent is detected.

BRIEF DESCRIPTION OF THE DRAWINGS

These and other objects of the present invention will become clear from the detailed description set forth hereinafter taken in conjunction with the drawings, wherein:

FIG. 5 is a vertical section showing a presently preferred test sample chamber employed in the systems of FIGS. 1, 2 and 3;

FIG. 6 is a vertical section showing a presently preferred mixing chamber for mixing sample solution with either diluent or reagent in the systems of FIGS. 2 and 3;

FIG. 7 is a diagrammatic view illustrating alternative apparatus for accurately measuring a predetermined quantity of diluent or reagent in the systems of FIGS. 2 and 3; and FIG. 8 is a greatly enlarged fragmentary sectional view taken on the line 8—8 in FIG. 4, illustrating the novel filter stop device of the present invention and a means for mounting same.

DETAILED DESCRIPTION

Figure 1:
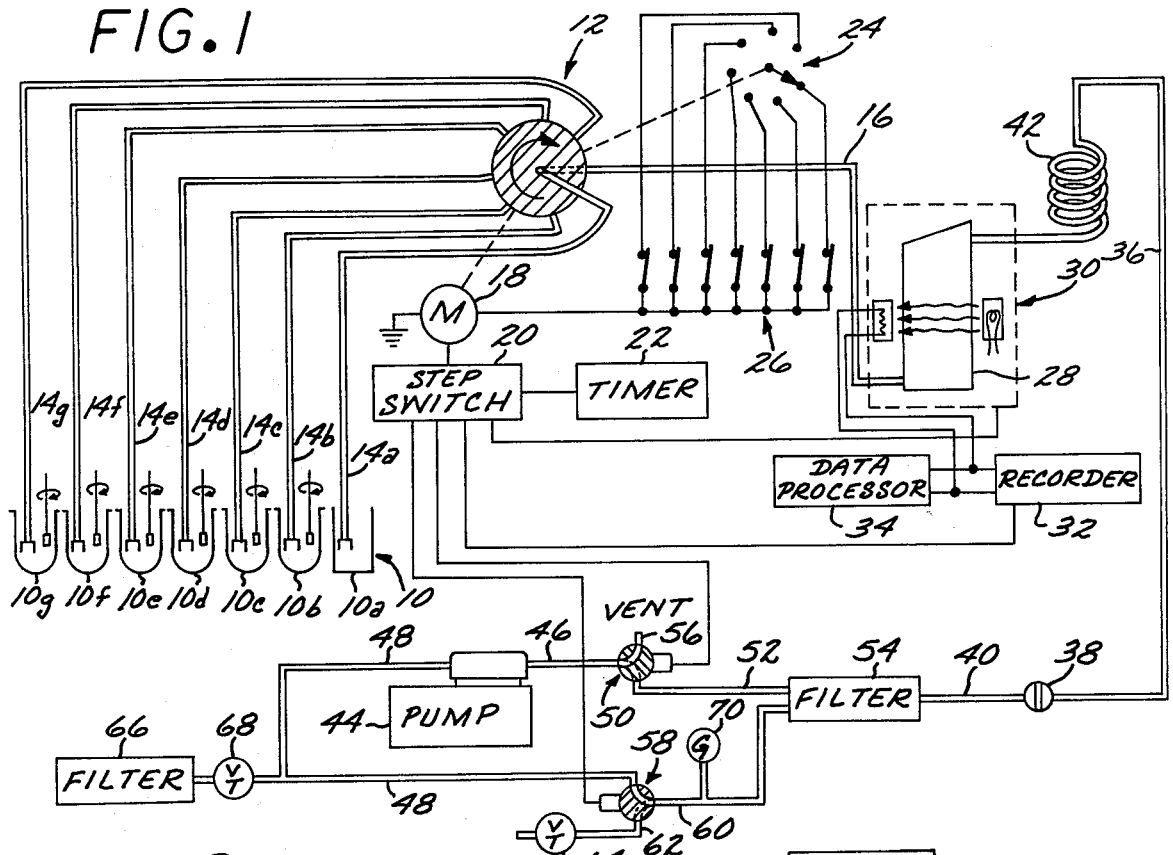
FIG. 1 is a diagrammatic illustration of a simplified form of the invention adapted for multiple sample dissolution rate testing, wherein sample solutions are tested without the addition of a diluent or reagent.

FIG. 1 of the drawings illustrates a simplified form of the invention which embodies the basic bi-directional flow system without the means for adding a diluent or reagent to the samples that are to be tested. In the basic system of FIG. 1 only a single access conduit is required for each of a series of sample chambers, with the sample alternately being withdrawn by vacuum from the chamber through its respective access conduit for testing, and then the sample being returned by air pressure to the chamber through the same access conduit, with the pressure being continued after return of the sample so as to purge the conduit and associated filter. This enables the dual intake and output tubes and dual sequencing valves of conventional systems to be eliminated, and also permits elimination of the conventionally required peristaltic pump. Further, this novel bi-directional flow system permits complete purging of all of the sample from the conduits of the system, thereby avoiding crossover with the next sample in sequence to be tested.

A series of sample chambers containing the samples to be tested and also a reference sample is generally designated 10, and in the embodiment shown the sample chambers 10 include a reference sample chamber 10a and six test sample chambers or flasks 10b–10g. Although any number of test sample chambers may be provided, the typical number employed will be six because for pharmaceutical dissolution rate testing, official dissolution procedure No. 1 defined in the U.S. Pharmacopea specifies that six tests must be run on any dosage form where testing is required. Dissolution apparatus is employed in association with the six test sample chambers 10b–10g, such as Multiple Spindle Basket Stirrer Drive Model 72 available from Hanson Research Corporation of Northridge, Calif., or the "spin filter" apparatus disclosed in U.S. Pat. No. 3,801,280. If the apparatus is to be employed for uniformity testing, twenty test samples will normally be required instead of six.

A seven-way sample selector valve 12 is provided which is a step valve having seven sample access ports which communicate with the respective sample chambers 10a–10g through respective sample access tubes 14a–10g. In the seven positions of sample selector valve 12, the valve 12 provides communication between the respective sample access tubes 14a–14g and a single sample delivery conduit 16. The selector valve 12 is sequentially shifted from position to position by means of a step motor 18 which is started from one position to the next by a step switch 20, the motor 18 automatically shutting itself off at such next position of the valve 12. Step switch 20 may conveniently be of the multiple layer type commonly referred to in the art as a "water switch". Step switch 20 is energized by means of a timer 22 which is preferably, but not necessarily, a solid state digital timer of a conventional type having an adjustably programmable timing sequence.

A step switch 24 for automatically stopping the step motor 18 at each of the seven positions of sample selector valve 12 is diagrammatically shown, and a series 26 of seven normally closed sample bypass switches 26 is connected to the step motor stop switch 24. By opening one or more of the bypass switches 26 in sequence, the sample selector valve 12 will be moved by step motor 18 past the positions corresponding to the open bypass switches 26 and will stop at the position corresponding to the next closed bypass switch 26. For example, if desired by opening all of the intermediate sample bypass switches 26, the sample selector valve 12 can be moved all of the way from communication with sample access tube 14a to communication with sample access tube 14g without stopping at any of the intermediate sample access tubes.

Sample delivery conduit 16 communicates with the flow cell 28 of a sample concentration detector generally designated 30 which may be any type of concentration detector common in the art, as for example a spectrophotometer which measures ultraviolet light absorbence, a fluorometer which measures fluorescence, or the like. Examples of suitable concentration detectors currently available on the market are the Beckman Model 25 spectrophotometer and the Turner fluorometer equipped with flow cell. Detector 30 has an electrical output that is connected to a recorder 32 which is preferably but not necessarily of the bar graph type. The electrical output of detector 20 may also be connected to a data processor 34 if desired.

An overflow conduit 36 leads from flow cell 28 to one side of a filter stop device 38, the other side of which connects with pressure/vacuum conduit 40 to which pressure and partial vacuum are alternately applied pursuant to a sequence determined by timer 22 and stop switch 20. The flow cell overflow conduit 36 preferably includes an excess sample storage loop 42 located between flow cell 28 and filter stop 40 to assure adequate conduit length to entrap any bubbles that may form in the flow cell. It is to be noted that the sample delivery conduit 16 connects proximate the bottom of flow cell 28, while the overflow conduit 36 connects proximate the top of flow cell 28, with excess sample storage loop 42 extending upwardly from this latter connection.

The filter stop device 38 faces toward overflow conduit 36 and flow cell 28, and is characterized by the ability to completely block the passage of liquid coming from the direction that the filter stop faces under the amount of pressure differential applied by vacuum in pressure/vacuum conduit 40. On the other hand, the filter stop device 38 has the characteristic of allowing the free passage of air or other gas in either direction with minimal pressure drop across the filter stop. The construction and materials of the filter stop device 38 are described in detail hereinafter in connection with FIG. 8 of the drawings.

If the flow cell overflow conduit 36 has sufficient volume therein to assure that none of the sample fluid can be drawn by vacuum into the air pump which applies the pressure or vacuum to pressure/vacuum conduit 40, then the filter stop device 38 may optionally be omitted from the simplified form of the invention shown in FIG. 1. However, it is nevertheless preferred to include the filter stop device 38 as a positive stop means for preventing any sample liquid from entering the air pump or any of the valves and lines immediately associated with the pump, so as to prevent crossover with the next sample liquid in sequence.

The air pump 44 may be a diaphragm or other conventional type of air pump, and need not be a pump of the peristaltic type which has heretofore been required in automatic dissolution rate determining apparatus. Air pump 44 is adapted to continuously operate, and it has a pressure output conduit 46 and a vacuum intake conduit 48. Pressure conduit 46 from the pump is connected through two-way pressure air valve 50, pressure conduit 52 and filter 54 to the pressure/vacuum conduit 40. In the dotted line position of pressure air valve 50, air pressure is supplied by pump 44 through conduit 46, valve 50, conduit 52 and filter 54 to the pressure/vacuum conduit 40. In the solid line position of pressure air valve 50, the air pressure from pump 44 is vented through vent port 56 of valve 50.

Pump vacuum intake conduit 48 is connected to two-way vacuum air valve 58, vacuum conduit 60 and filter 54 to the pressure/vacuum conduit 40 when vacuum air valve 58 is in its solid line position. When vacuum air valve 58 is in its dotted line position, vacuum conduit 60 is connected to exhaust port 62 of vacuum air valve 58 which is vented to atmosphere through pressure adjust needle valve 64 which adjustably controls the pressure that is applied to pressure/vacuum conduit 40 when both valves 50 and 58 are in their dotted line positions.

Both of the air valves 50 and 58 are preferably solenoid actuated for substantially instantaneous shifting from one position to the other.

Intake air is supplied to pump 44 through air intake filter 66 and vacuum adjust needle valve 68 that connects with vacuum intake conduit 48. The amount of partial vacuum applied to pressure/vacuum conduit 40 when valves 50 and 58 are in their solid line positions is adjustably controllable by the needle valve 68, and is indicated on a vacuum gauge 70 that is connected to vacuum conduit 60.

Operation of the simplified embodiment shown in FIG. 1 is most conveniently described with reference to the sequence of positions of step switch 20 as programmed by timer 22. When step switch 20 is shifted by timer 22 to position 1 of a new operational sequence, step switch 20 will cause sample selector valve 12 to shift to a new sample in one of the sample chambers 10a–10g through the respective sample access tube 14a–14g. In this first position of step switch 20 the step switch 20 does not shift either of the air valves 50 and 58 which remain in their previous positions hereinafter referred to as the "purge" positions of the air valves, wherein air valves 50 and 58 are both in the dotted line position providing air pressure to pressure/vacuum conduit 40 and hence to the system. During the preceding position of step switch 20, with air valves 50 and 58 thus in their dotted line purge position, overflow conduit 36, flow cell 28, delivery conduit 16, selector valve 12 and the previous sample access tube and associated filter were completely purged of liquid and are therefore filled with air when step switch 20 shifts to position 1.

The dwell timme of step switch 20 in position 1 is set by timer 22 to be sufficiently long to allow selector valve 12 to cycle from the previous sample access port all of the way past five access ports to the sixth access port should the next five of the sample bypass switches 26 be open. A presently commercially available seven-way valve suitable for the sample selector valve 12 (Part No. 202-00-9 from Altex Scientific, Inc., Berkeley, Calif.) requires approximately 7½ seconds to cycle around to the sixth access port, so with such sample selector valve 12 the dwell time for step switch 20 in position 1 is preferably fixed at 8 seconds. Thus, regardless of which sample is selected as the new sample by the bypass switches 26, when sample selector valve 12 arrives at the new sample access tube, a shot of air pressure will be applied through the newly selected sample access tube to purge the filter for the newly selected sample of any solid material that may have accumulated while that sample was idle, this air pressure shot occurring because the air valves 50 and 58 are in their dotted line purge positions.

Step switch 20 is then shifted by timer 22 to position 2 which may be referred to as the "fill" position. Timer 22 is preferably programmable to select a dwell time for step switch 20 in position 2 of from 0 to 99 seconds. The dwell time will be selected as a function of tube length in the system and viscosity of the sample liquid, a normal dwell time for the fill position being about 20 seconds.

When step switch 20 shifts to position 2 the two air valves 50 and 58 are shifted by step switch 20 to their solid line positions which is "fill" condition of the valves 50 and 58. The sample selector valve 12 remains in the new sample position to which it was shifted in position 1 of step switch 20. In this fill condition of air valves 50 and 58, vacuum as adjusted by needle valve 68 is applied from vacuum intake conduit 48 through air valve 58, vacuum conduit 60, filter 54, pressure/vacuum conduit 40 and filter stop device 38 to the flow cell overflow conduit 36, and thence through flow cell 28, sample delivery conduit 16, sample selector valve 12 and the respective sample access tube to the new sample chamber of the chambers 10a–10g. This vacuum in the system draws the new sample from the sample chamber out through the respective filter and sample access tube, selector valve 12, delivery conduit 16 and into the flow cell 28, filling the flow cell 28 and overflowing into the overflow conduit 36. Inasmuch as some bubbling may occur in flow cell 28, it is important that the flow of the new sample liquid move materially beyond flow cell 28 into the overflow conduit 36 so as to assure that any such bubbles will be shifted out of flow cell 28 into overflow conduit 36. This is an important aspect of the invention, inasmuch as any substantial bubble content within flow cell 28 when the sample concentration is being read by detector 30 will adversely affect the reading.

During this second or fill position of step switch 20, the filter stop device 38 freely allows the air to be evacuated from the system but provides a positive stop against any of the liquid sample passing back to the pump 44 or any of its immediately associated conduits or valves.

At the end of the fill part of the operational sequence, step switch 20 is shifted by timer 22 to position 3, wherein step switch 20 shifts vacuum air valve 58 to its dotted line vent position, the pressure air valve 50 remaining in its previous position which was its solid line vent position. Thus, in position 3 of step switch 20 both of the air valves 50 and 58 are in the vent or idle position. Sample selector valve 12 remains in the same position to which it was shifted in position 1 of step switch 20.

The dwell time for position 3 is relatively short, preferably about 8 seconds. There is no flow in the system at this time, and the purpose of this step in the sequence is to allow the system, and particularly the contents of the flow cell, to stabilize, with pressure equalization occurring, in preparation for the next step in the sequence, which is the "read-record" step.

Step switch 20 is next shifted by timer 22 to position 4, the "read-record" position which has a dwell time preferbly selectively adjustable by timer 22 to be from 0 to 99 seconds, although a record-record dwell time of about 5 seconds will normally be adequate. In position 4 the step switch 20 energizes detector 30 and recorder 32 so that the concentration of the sample in flow cell 28 is read by the detector 30 and recorded by the recorder 32. The step switch 20 is preferably arranged to cause the recorder 32 to be shorted in all other positions of step switch 20 so as to avoid the recording of any spurious signals during those portions of the operational sequence in which the recorder is inactive.

There is no change in the positions of air valves 50 and 58 and sample selector valve 12 when step switch 20 shifts from the stabilization position 3 to the read-record position 4, and accordingly there is no flow in the system during the read-record phase of the sequence. Inasmuch as position 4 of switch 20 is simply a continuation or extension of position 3 insofar as the valves are concerned, the only difference being the reading and recording which occurs in position 4, these two positions of step switch 20 can be combined into a single position wheren the shifting of air valve 58 to its dotted line vent position and the energization of detector 30 and recorder 32 are to occur simultaneously.

At the end of the read-record phase of the operational sequence the timer 22 energizes step switch 20 to shift step switch 20 into position 5 which is a purge pressure buildup phase of the operational sequence having a dwell time preferably of about 8 seconds. As step switch 20 shifts from position 4 to position 5, the read-record phase ends and the recorder is again shorted to prevent the recording of any spurious signals, as it was during positions 1-3 of step switch 20. In position 5 the step switch 20 shifts pressure air valve 50 from its solid line vent position to its dotted line pressure position, but step switch 20 leaves vacuum air valve 58 in its previous vent or dotted line position, wherein the needle valve 54 is adjustable to adjust the purge pressure applied by pump 44 through conduit 46, valve 50, conduit 52, filter 54, conduit 40 and filter stop device 38 to the flow system starting at flow cell overflow conduit 36.

At the end of the pressure buildup phase of the operational sequence as represented by position 5 of step switch 20, the timer 22 again energizes step switch 20 to shift step switch 20 to position 6 which is the "purge" phase of the operational sequence. Timer 22 is preferably adjustable to select a dwell time for position 6 of step switch 20 from 0 to 99 seconds, the normal dwell time for the purge phase being about 30 seconds. In purge position of step switch 20 air valve 50 remains in it previous position, which is the dotted line pressure position; air valve 58 remains in its previous position, which is the dotted line position; and sample selector valve 12 remains in the position to which it was shifted in position 1 of step switch 20, the sample selector valve 12 remaining in this same position throughout positions 2 through 6 of step switch 20.

During the purge phase of the operational sequence as determmined by position 6 of step switch 20, air under pressure forces all of the liquid sample that has just been measured for concentration back through flow cell overflow conduit 36, flow cell 28, sample delivery conduit 16, sample selector valve 12, and the respective sample access tube in the series of tubes 14a-14g, and then through the respective filter at the end of the access tube into the respective sample chamber of the series of sample chambers 10a-10g.

The purge phase is set by adjustment of timer 22 to last sufficiently long so that substantially all of the sample that has just been measured is returned to its respective sample chamber, with all of the flow passages being substantially completely cleared of such sample to minimize carryover or crossover with the next sample to be measured. In practice, it has been found that such carryover or crossover is normally less than 1% and as low as 1/10% in the apparatus of FIG. 1.

Since positons 5 and 6 of step switch 20 provide the same valve positions in the apparatus, position 5 of step switch 20 and its associated fixed pressure buildup time may be omitted froom the operational sequence, and the step switch 20 may shift direectly from position 4 (read-record phase) to position 6 (purge phase of selectable dwell time). However, it is preferred to include the purge pressure buildup phase of step switch position 5 so as to assure that at least 8 seconds of pressure buildup and purging occur regardless of the dwell time that is selected from the purge phase of step switch position 6.

Figure 2:
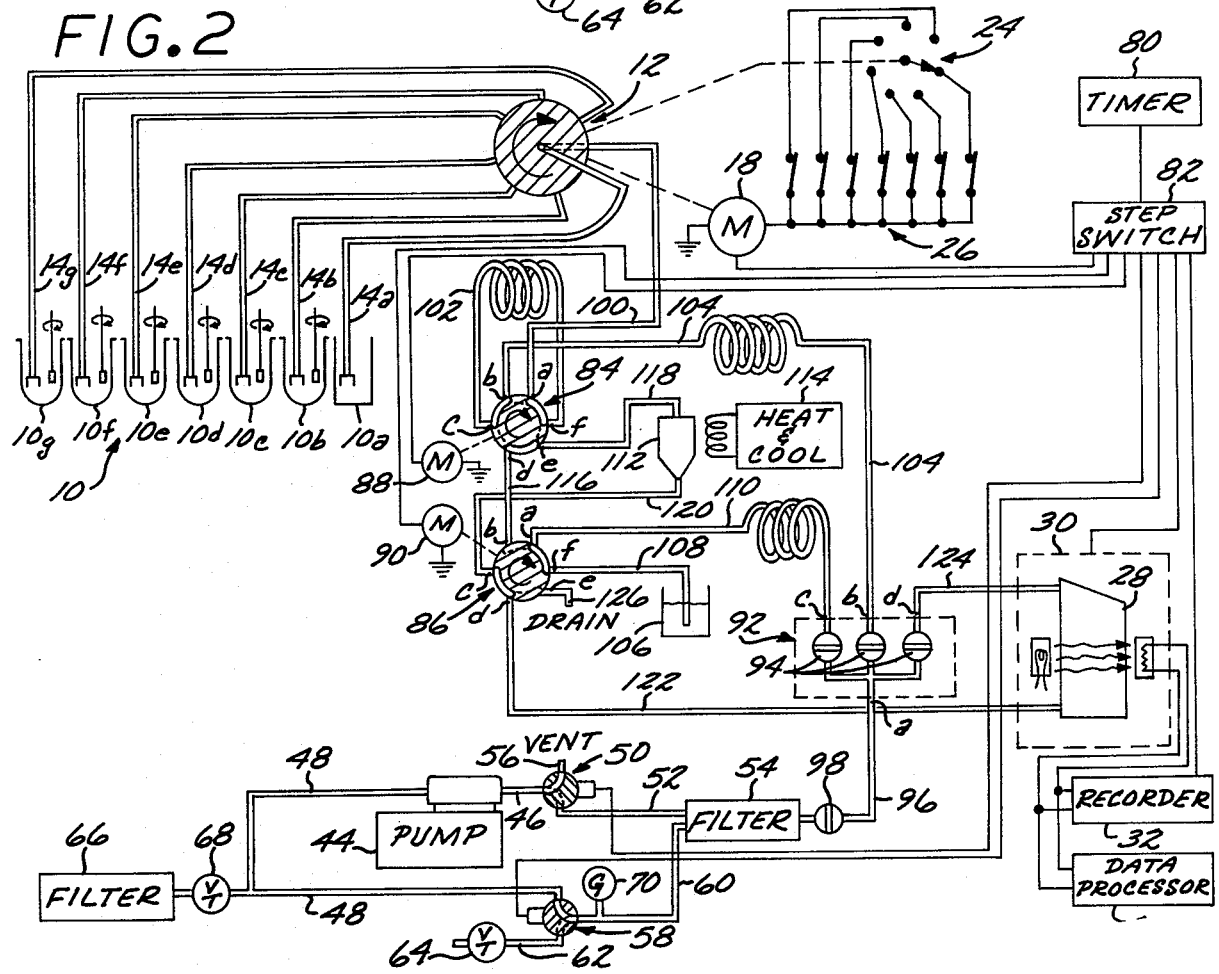
FIG. 2 is a diagrammatic view similar to FIG. 1, but including additional apparatus for adding to and mixing with the sample solution an accurate proportion of a diluent or a reagent so as to make the concentration of the sample compatible with the concentration detector.

FIG. 2 illustrates apparatus which is essentially the same as the apparatus of FIG. 1, but with additional valves, conduits and fluid handling apparatus embodied in the system so as to enable an accurately measured proportion of diluent to be added to and mixed with each of the samples in sequence in the event that the sample without dilution is too concentrated for accurate measurement by the concentration detector. Conversely, this same system of FIG. 2 may be employed to add to and mix with each sample an accurately measured proportion of a reagent in the event the sample is not sufficiently concentrated for an accurate reading by the concentration detector, the reagent being such as to react with the sample solution so as to render the solution optically more readable.

Referring now to the details of the system illustrated in FIG. 2, the sample chambers 10a-10g, seven-way sample selector step valve 12, sample access tubes 14-14g step motor 18 for actuating selector valve 12, and step motor stop switch 24 and associated sample bypass switches 26 may all be the same as the similarly numbered elements of FIG. 1. Likewise, in the system of FIG. 2 the pump 44 and air valves 50 and 58, and the associated conduits 46, 48, 52, 60 and 62 may be the same as the similarly numbered elements in the system of FIG. 1, as well as the associated filters 54 and 66, needle valves 64 and 68, and vacuum gauge 70. Further, the sample concentration detector 30 and its flow cell 28, and recorder 34 and data processor 36, FIG. 2 may be the same as the similarly numbered elements in the system of FIG. 1. However, timer 80 and step switch 82 in the system of FIG. 2 involve more functions than timer 22 and step switch 20 in the system of FIG. 1 so as to accommodate two additional step valves and associated fluid dircuits included in the system of FIG. 2. These are control valves 84 and 86, each of which has six ports $a$-$f$. Control valves 84 and 86 are actuated by respective step motors 88 and 90 which in turn are energized by step switch 82 according to the timing sequence that is programmed into timer 80. The control valves 84 and 86 are adapted to be cycled between two positions, a "fill" position shown in solid lines, and a "purge" position shown in dotted lines. Each of the control valves 84 and 86 is arranged to shift 300° in a clockwise direction as shown from the solid line fill position to the dotted line purge position, and to shift 60° clockwise from the dotted line purge position back to the solid line fill position. While the construction of control valve 84 is such that it could be arranged to simply shift 60° in each step, the 300°-60° shift sequence is preferred to minimize carryover in the valve. Since the control valves 84 and 86 are shifted synchronously in the 300° and 60° increments, they could be mechanically coupled and actuated by a single step motor; however, to simplify replacements of parts in the field, it is preferred that the control valves 84 and 86 be separately actuated by respective step motors 88 and 90.

The pressure/vacuum source in the system of FIG. 2 communicates with a manifold generally designated 92 which has a single port 92a in communication with the pressure/vacuum source, the single manifold port 92a in turn communicating with three manifold ports 92b, 92c and 92d, each of which has in its flow path a filter stop device 94 which faces toward the flow system or away from the pressure/vacuum source so as to positively stop any liquid flow in the direction toward the pressure/vacuum source, but to freely allow the flow of air or other gas in either direction. Pressure/vacuum conduit 96 provides communication from pressure conduit 52 and vacuum conduit 60 through filter 54 to the manifold port 92a. An additional filter stop device 98 is preferably disposed in pressure/vacuum conduit 96 facing toward manifold 92 is a positive barrier against liquid flow back to pump 44 and its immediately associated valves and conduits in the event one of the three filter stop devices 94 should inadvertently be omitted during servicing of the apparatus.

The sample delivery conduit 100 of the system illustrated in FIG. 2 leads from the seven-way sample selector valve 12 to control valve 84 port a. A sample measure loop conduit 102 is connected at one end to control valve 84 port f, and at its other end to control valve 84 port c. Excess sample conduit 104 then leads from control valve 84 port b to manifold port b.

A diluent/reagent supply chamber 106 is provided which is adapted to contain either a diluent liquid or a reagent liquid to be mixed with each sample as required to bring the absorbence of the sample with the accurate range of sample concentration detector 30.

The system illustrated in FIG. 1 requires a detector 30 which can be adjusted to provide an accurate reading from whatever concentration of chemical happens to be in each of the dissolution chambers 10a–10g. However, in some types of testing, such as pharmaceutical testing, this sample chemical concentration is fixed and cannot be selected by the operator. For example, if the operator is testing a certain pharmaceutical tablet containing a discrete amount of a given drug, he is required to do so in a volume of solvent that is comparable to that volume which the tablet might encounter in the human system in order to come as close as possible to the biological parameters of drug availability. In addition to such requirement, the operator is also limited by the sheer physical volumes involved. For example, standard dissolution apparatus and techniques recommend one liter of diluent per chamber which involves sample chambers 10a–10g of practical dimensions, but if the tablet or other drug uniti being test should in one liter of diluent produce ten times the concentration of the detector range, then the operator would be required to dilute the drug unit in ten liters and dissolution fluid to come within the detector range, and this would require dissolution chambers of unmanageably large size, and in addition the given dosage form would then be subjected to ten times the solvent interface which would change the parameters of the test. The prior art method of solving this problem was to utilize different flow cell volumes. Thus, in the example given where the concentration was ten times too great, the standard flow cell having a 10 mm. path would be replaced by a flow cell having a 1 mm. flow path. This prior art approach is expensive and inconvenient, and since flow cells are only available in a few discrete sizes it is difficult to continuously adjust the flow cell light path until the range of the detector is reached. Another prior art solution to this problem was to withdraw the sample into a separate container and process it independently of the automated system, but this results in an undesirable interruption of the automated system.

These problems are completely overcome by the novel system of FIG. 2 wherein an accurately measured quantity of diluent from the supply chamber 106 is added and mixed with an accurately measured quantity of the sample solution to bring the resulting mixture within the accurate range of sample concentration detector 30. The system of FIG. 2 has the further important advantage that if on the other hand the concentration of the sample solution should be too weak to come within the range of detector 30, then a reagent may be employed in the supply chamber 106 for addition and mixing in an accurate quantative ratio with the sample solution to bring the optical density of the sample solution up to within the range of the detector 30.

A desired quantity in desired proportions for filling flow cell 28 and obtaining an accurate reading by detector 30 of the sample solution on the one hand and diluent or reagent on the other hand is obtained by first filling the sample measure loop 102 with sample and filling the diluent/reagent measure loop 110 with diluent or reagent, and then moving these measured quantities of liquids into the mixing chamber 112 and mixing them, and subsequently moving the mixture of the measured liquids into the flow cell 28 and reading the concentration of the mixture in detector 30 and recording the results on recorder 34. Optimum dilution for minimum carrover or crossover of only about 1–2% between successive samples if about 5–1. although satisfactory results are achievable with dilutions up to as much as 20–1 or more.

The step switch 82 in FIG. 2 as actuated by the adjustably programmable timer 80 preferably has six sequential positions which are functionally similar to the corresponding six preferred positions of step switch 20 in FIG. 1, but which perform some additional functions in the operative sequence of the system of FIG. 2, as will be understood from the following description of such operative sequence.

When timer 80 applies a timing pulse to step switch 82 to shift step switch 82 to position 1 so as to start a new operative sequence, the seven-way sample selector valve 12 is caused by step switch 82 to shift to a new sample, which could be any one of the next samples in sequence according to the positioning of the bypass switches 26. Step switch 82 simultaneously energizes step motors 88 and 90 which cycle respective control valves 84 and 86 to new positions which are the "fill" positions shown in solid lines in FIG. 2. When step switch 82 thus shifts to position 1 it leaves the two air valves 50 and 58 in their previous positions, which are the dotted line "purge" positions wherein pump 44 is applying pressure to the system. The dwell time, for example a fixed 8 seconds, for step switch 82 in position 1 is sufficient for complete cycling of control valves 84 and 86 to their new positions, and for complete cycling of sample selector valve 12 to whatever new sample is selected, with sufficient additional time for a pressure shot to pass through the previously purged conduits and then through the selected sample access tube of the tubes 14a–14g so as to dislodge any accumulated clogging from the respective sample access filter. This pressure shot will be applied from pump 44 through conduit 46, air valve 50, conduit 52, filter 54, filter stop 98, conduit 96, manifold 92 ports a and b and the respective filter stop 94, excess sample conduit 104, control valve 84 ports b and c, sample measure loop 102, control valve 84 ports f and a, sample delivery conduit 100, selector valve 12 and the respective sample access tube of the tubes 14a–14g.

In position 1 of step switch 82 there is also a reverse air pressure shot which bubbles up into mixing chamber 112 to assist in mixing the sample and diluent or reagent which were moved into mixing chamber 112 during the immediately preceding purge phase. This reverse air flow up into mixing chamber 112 is supplied from pump 44 through manifold 92 port d and previously purged conduit 124, flow cell 28, conduit 122, control valve 86 ports d and c, and mixing chamber outlet conduit 120.

Step switch 82 is next shifted by timer 80 to position 2, which will be referred to as the "fill" position, position 2 having a dwell time that is selectable by adjustment of timer 80 between 0 and 99 seconds according to tube length and liquid viscosity, with a normal dwell time for the fill phase being about 20 seconds.

In position 2 the step switch 82 shifts air valves 50 and 58 from their dotted line pressure or purge positions to their solid line vacuum or fill positions. In position 2 of step switch 82 the selector valve is left in its previous new sample position, and control valves 84 and 86 are left in their previous solid line fill positions. Vacuum is applied from pump 44 through conduit 48, air valve 58, conduit 60, filter 54, filter stop 98, and conduit 96 to manifold 92 port $a$ and hence ports $b$, $c$ and $d$ through respective filter stops 94. Vacuum from manifold 92 port $b$ is applied through excess sample conduit 104, control valve 84 ports $b$ and $c$, sample measure loop 102, control valve 84 ports $f$ and $a$, sample delivery conduit 100 and selector valve 12 to draw the new sample solution from the respective sample chamber and access tube into this flow path so as to solidly fill the sample measure loop 102 with the sample solution and pull a sufficient amount of the sample solution into excess sample conduit 104 so that any bubbles in the sample solution will be pulled on through the sample measure loop 102 into excess sample conduit 104.

Vacuum will simultaneously be applied from manifold 92 port $c$ through diluent/reagent measure loop 110, control valve 86 ports $a$ and $f$ and diluent/reagent supply conduit 108 to the supply chamber 106, drawing diluent or reagent from supply chamber 106 through this flow path to the filter stop 94 associated with manifold 92 port $c$ so as to solidly fill the diluent/reagent measure loop 110 with diluent or reagent as the case may be.

Vacuum will simultaneously be applied from manifold 92 port $d$ through flow cell pressure/vacuum conduit 124, flow cell 28, flow cell feed conduit 122, control valve 86 ports $d$ and $c$, and mixing chamber outlet conduit 120 to the mixing chamber 112 so as to draw the mixture of the previous sample and diluent or reagent from mixing chamber 112 through this flow path, filling flow cell 28 with the previous sample mixture, which overflows into conduit 124 and is stopped at the respective filter stop 94 associated with manifold 92 port $d$. Conduit 124 is sufficiently long to receive any bubbles which may have formed as a result of churning of the mixture as the mixture fills the flow cell 28, so that flow cell 28 is solidly filled with the liquid mixture and no substantial bubble content will be present in flow cell 28 to interfere with an accurate reading of the mixture of sample solution and diluent or reagent.

Step switch 82 is next shifted by timer 80 to position 3 in which step switch 82 shifts vacuum air valve 58 from its solid line vacuum position to its dotted line vent position, and shifts both of the control valves 84 and 86 from their solid line fill positions to their dotted line purge positions, the sample selector valve 12 remaining in its previous new sample position. Position 3 of step switch 82 has a dwell time preferably of about 8 seconds, during which the system, and in particular the flow cell contents, is allowed to stabilize, with pressure equalization occurring, in preparation for the "read-record" part of the operational sequence which will occur next.

Step switch 82 is next shifted by timer 80 to position 4 which is the "read-record" position, with a dwell time selectable by adjustment of timer 80 preferably from 0 to 99 seconds, with a normal read-record dwell time of about 5 seconds. Position 4 of step switch 82 is simply an extension of position 3, with all of the valves remaining in their condition of position 3 of step switch 82. In position 4 of step switch 82 the detector 30 is energized to take a concentration reading of the previous sample that is present in flow cell 28, and recorder 32 is unshorted for recording of this sample concentration reading (recorder 32 having been shorted in all other positions of step switch 82 to avoid any spurious signal recordings).

Step switch 82 is next shifted by timer 80 to position 5 which is the purge pressure buildup phase of the operational sequence. In position 5 of step switch 82 detector 30 is again de-energized, recorder 32 is again shorted, pressure air valve 50 is shifted from its solid line vent mode to its dotted line pressure mode, and air valve 58 remains in its dotted line vent position. Sample selector valve 12 remains in its previous new sample position, and control valves 84 and 86 remain in their previous purge positions. Position 5 of step switch 82 has a preferred fixed dwell time of about 8 seconds, and assures satisfactory purge pressure buildup and some purging of the lines regardless of dwell time that is selected for the fixed and final "purge" phase of the operational sequence that will occur next.

Step switch 82 is then shifted by timer 80 to position 6 which has a preferred dwell time of from 0 to 99 seconds selectable by adjustment of timer 80, with a normal dwell time for the purge phase of about 30 seconds. All of the valves remain in the same condition as for position 5 of step switch 82, and operation of the system during this purge position 6 of step switch 82 is as follos:

Air pressure applied through manifold 92 port $b$ purges liquid from the path including excess sample conduit 104, control valve 84 ports $b$ and $a$, sample delivery conduit 100, selector valve 12 and the new sample access tube and its filter that were selected in position 1 of step switch 82 for this operative sequence of the system. This reverse flow of sample solution and air substantially completely clears these conduits of liquid and cleans the respective filter of particulate material, and this returns all of the new sample solution to its respective sample chamber except for that amount of sample solution which has been captured in sample measure loop 102.

Air pressure applied through manifold 92 port $d$ purges the previous mixture of sample solution and diluent or reagent from flow cell pressure/vacuum conduit 124, flow cell 28 and flow cell feed conduit 122 through control valve 86 ports $d$ and $e$ to drain conduit 126, thus removing the previous mixture from the system.

Air pressure applied through manifold 92 port $c$ moves the accurately measured quantity of diluent or reagent from its measure loop 110 through control valve 86 ports $a$ and $b$, diluent/reagent feed conduit 116 and control valve 84 ports $d$ and $c$, and them moves this measured quantity of diluent or reagent together with the measured quantity of the new sample solution through sample measure loop 102, control valve 84 ports $f$ and $e$ and mixing chamber feed conduit 118 to the mixing chamber 112, where the new mixture of sample solution and diluent or reagent are mixed together as they flow into and are received in mixing chamber 112, and are further mixed by the reverse flow of air under pressure up into the bottom of mixing chamber 112 through its outlet conduit 120 during the first phase of the next operative sequence of the system as explained hereinabove. This new mixture in mixing chamber 112 may be heated or cooled by temperature controller 114 for optimum reading in the sample concentration detector 30 during the fourth or read-record phase of the next opertive sequence of the system.

As with the system of FIG. 1, the system of FIG. 2 may alternatively be operated with either only four phases or only five phases, by combining the pressure stabilization and equalization phase three with the read-record phase four, and/or combining the purge pressure buildup phase five with the purge phase six.

Figure 3:
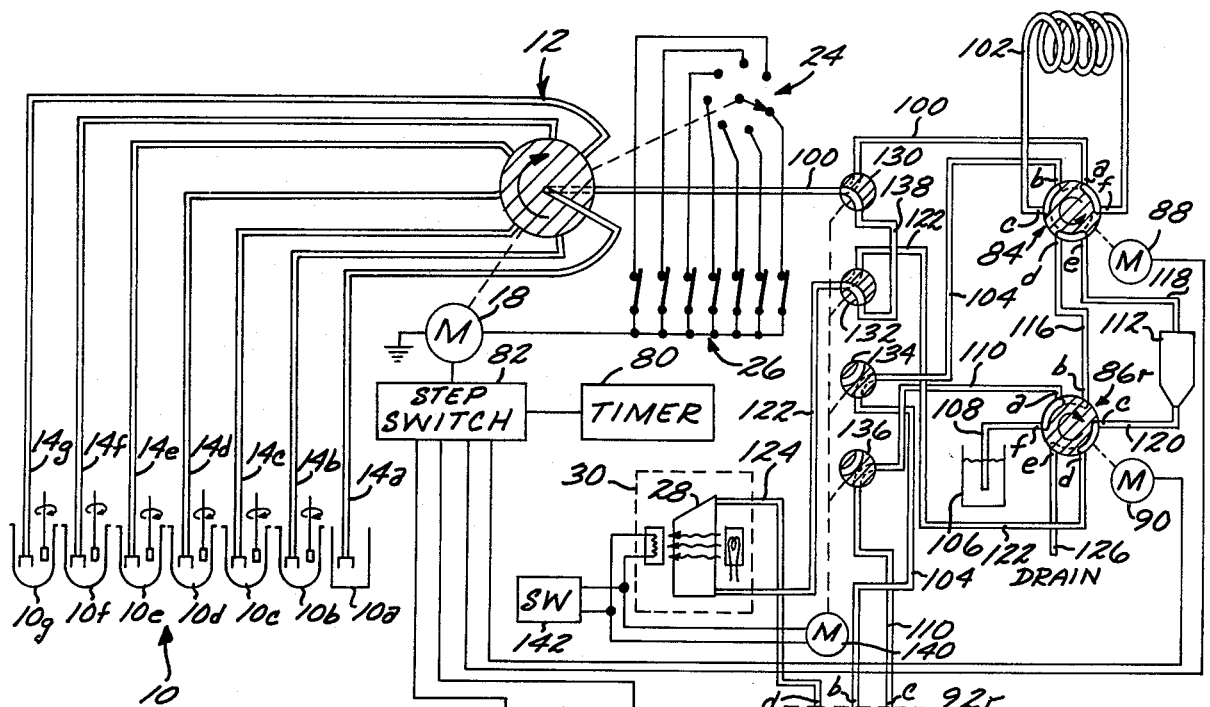
FIG. 3 is a diagrammatic view similar to FIG. 2, but with the addition of valving which enables the system to be selectively shifted between the direct sample mode of FIG. 1 and the sample mixture mode of FIG. 2.

FIG. 3 illustrates the same system as shown in FIG. 2, but with the addition of four "mode shift" valves 130 132, 134 and 136 which are adapted to shift the system between two alternative modes of operation, the direct sample mode of FIG. 1 wherein the sample solution is directly provided at full strength to the flow cell, and the dilution/reaction mode of FIG. 2 wherein a measured proportion of diluent or reagent is added to the sample solution for mixing and delivery to the flow cell. For simplicity, the recorder 32 and data processor 34 have been omitted from FIG. 3, although it is to be understood that they are connected in the system as in FIGS. 1 and 2. Also, for convenience in the illustration, the control valve 86 and the manifold 92 of FIG. 2 have been reversed in FIG. 3, being designated control valve 86r and manifold 92r, respectively, in FIG. 3.

Mode shift valve 130 is interposed in sample delivery conduit 100 of FIG. 2; mode shift valve 132 is interposed in flow cell feed conduit 122 of FIG. 2; mode shift valve 134 is interposed in excess sample conduit 104 of FIG. 2; and mode shift valve 136 is interposed in diluent/reagent measure loop 110 of FIG. 2. The solid line positions of mode shift valves 130, 132, 134 and 136 in FIG. 3 is direct sample mode, wherein the sample solution is drawn directly into flow cell 28 through sample delivery conduit 100, mode shift valve 130, conduit 138 between mode shift valves 130 and 132, the mode shift valve 132, and a portion of flow cell feed conduit 122, the conduit 124 serving the same function as flow cell overflow conduit 36 in the system of FIG. 1. In this direct sample mode, mode shift valve 134 blocks excess sample conduit 104 and mode shift valve 136 blocks diluent/reagent measure loop 110. In this direct sample mode the system of FIG. 3 has the same operational sequence as described in detail hereinabove for the system of FIG. 1.

The dotted line positions of mode shift valves 130, 132, 134 and 136 represent the dilution/reaction mode, wherein the bypass conduit 138 is blocked, and sample delivery conduit 100, flow cell feed conduit 122, diluent/reagent measure loop 110 and excess sample conduit 104 are unblocked so that the complete system of FIG. 2 is present. Thus, in the dotted line dilution/reaction mode positions of the mode shift valves 130, 132, 134 and 136 the system of FIG. 3 will have the same operational sequence as described in detail hereinabove for the system of FIG. 2.

The four mode shift valves 130, 132, 134 and 136 are adapted to be moved synchronously from one position to the other, and may be actuated by a step motor 140 in response to a signal derived from sample concentration detector 30. Thus, if the sample concentration should initially be considered satisfactory for direct sampling and the mode shift valves initially be in their solid line direct sample mode positions, and a sample should be too concentrated or too weak to come within the accurate range of detector 30, then the detector 30 may provide a signal to step motor 140 causing step motor 140 to shift the mode shift valves to their dotted line dilution/reaction mode positions so that as the sampling proceeds, diluent or reagent will be mixed with the sample solution to alter the concentration of the sample as provided to the detector 30 so that the detector 30 will be within its accurate range. Conversely, if the system is initiated in the dotted line dilution/reaction mode positions of the mode shift valves, then if the concentration of the mixed sample should prove too low in concentration because of the addition of a diluent or too high in optical density because of the addition of a reagent, than a signal from the detector 30 may be employed to actuate step motor 140 to shift the mode shift valves to their solid line direct sample mode positions.

Preferably a mode selector switch 142 is connected to the step motor 140 for manual selection of the mode of operation of the system as between the direct sample mode and the dilution/reaction mode.

Figure 4:
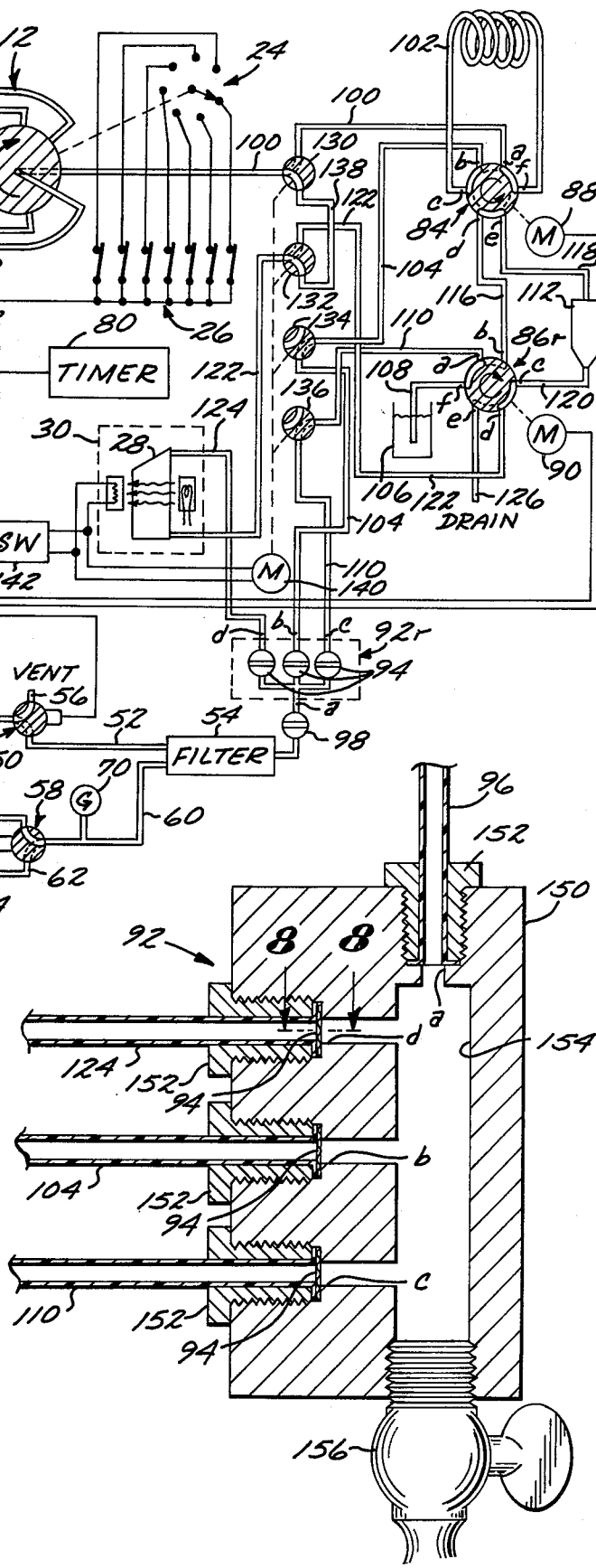
FIG. 4 is a cross-sectional illustration of the pressure/vacuum manifold employed in the systems of FIGS. 2 and 3.

FIG. 4 illustrates details of construction of a presently preferred manifold 92 which is simply diagrammatically illustrated in FIGS. 2 and 3. Manifold 92 includes a body 150 having ports 92a, 92b, 92c and 92d within which tubes of the respective conduits 96, 104, 110 and 124 are connected by means of suitable glands 152 that are threadedly engaged in the respective ports. Common manifold passage is in communication with each of the four ports 92a, b, c, and d, the common manifold passage 154 preferably being arranged generally upright so that any accumulated moisture may selectively be drained out of the bottom thereof through moisture drain petcock 156 disposed at the bottom of manifold body 150.

FIG. 5 illustrates one of the six test sample chambers employed in the systems of FIGS. 1, 2 and 3, as for example the test sample chamber 10b. A stirring basket 160 is shown containing a pharmaceutical tablet 162 to be tested, the stirring basket 160 and the tablet 162 being immersed in a suitable solvent which may be representative of a solvent that would be encountered by the tablet 162 upon injection into the human system. Although any desired type of stirring basket may be employed, a suitable stirring basket 160 may be of the type described and claimed in the William A. Hanson U.S. Pat. No. 3,572,648. Stirring basket 160 is supported in the solvent for rotational stirring on a rotatable shaft 166 which may be one of the spindles of a multiple spindle basket stirrer drive such as Hanson Research Corporation Model 72 referred to hereinabove, or other suitable stirring apparatus.

Although the present invention is particularly useful in pharmaceutical or other chemical dissolution rate testing, it is to be understood that it is equally adaptable for the testing of characteristics of any type of chemical for any desired purpose so that any type of chemical solution may be contained in the sample chamber 10b of FIG. 5. In the event that other types of testing are to be employed than dissolution rate testing, it will be understood that the detector 30 of FIGS. 1, 2 and 3 may comprise chemical testing apparatus suitable for testing chemical characteristics other than concentration.

The sample access tube 14b associated with test sample chamber 10b is connected just below the surface of the solution by means of a filter stop sleeve 168 to a generally vertically oriented, rigid tube 170 is vertically slidably supported in a bracket 172 attached to the wall of chamber 10b. The material of filter stop sleeve 168 is of the same character as the material of filter stop device 38 in FIG. 1 and filter stop devices 94 and 98 in FIGS. 2 and 3. The filter stop sleeve 168 in FIG. 5 has its filter stop layer facing radially outwardly so as to provide a positive barrier against the passage of the solution liquid into the tube under the applied amount of pressure differential, while nevertheless allowing the free passage of air or other gas from within the tube radially outwardly through the sleeve 168.

Disposed across the lower, input end of tube 170 is a filter disc 174 of conventional material which is mounted within a shell 176 supported at the lower end of tube 170, the disc 174 being secured in position by a hollow screw cap 178.

The solution pickup system shown in FIG. 5 is uniquely adapted to minimize aeration of the solution liquid during the purge phase of operation of the apparatus. Thus, while essentially all of the reverse liquid flow during the purge phase will pass downwardly through the sample access tube 14b, filter stop sleeve 168 and tube 170 through the filter 174 to clear the filter 174 of any captured particulate matter, most of the air or other gas that may pass downwardly through the sample access tube 14b during the purge phase will be diverted radially outwardly through the filter stop sleeve 168 proximate the upper surface of the solution so as to minimize bubbling throughout the body of the solution.

Bubbling during the purge phase is even further minimized by the provision of the vertically slidable mounting of rigid tube 170 in bracket 172, in combination with a slightly positive buoyancy of the tube 170 and its lower end apparatus 174, 176 and 178 when the tube 170 is partially filled with air or other gas, the tube 170 and its lower end apparatus having a slightly negative buoyancy when the tube 170 is solidly filled with the liquid solution. Thus, during the "fill" or suction mode of operation when sample solution is being withdrawn through filter 174, tube 170, filter stop switch 168 and sample access tube 14b, the tube 170 is solidly filled with the liquid solution and hence has negative buoyancy and will be in its lowermost position indexed by engagement of a stop member 179 on sleeve 170 against bracket 172, as illustrated in FIG. 5, and in this position the filter stop sleeve 168 will be immersed in the solution to avoid drawing any air into the system through the sleeve 168, In this position as shown in FIG. 5, all of the sample solution will be drawn into the sample access tube 14b through the filter 174, inasmuch as the filter stop sleeve 168 will positively block entry of any of the solution at that point.

During the "purge" mode of operation, the sleeves 168 and 170 will remain in the lowermost position of FIG. 5 while solid liquid flows back into the sample chamber 10b, but when a substantial amount of air or other gas is contained in the reverse flow, the positive buoyancy of tube 170 and its associated apparatus will cause tube 170 and filter stop sleeve 168 to rise to a position wherein filter stop sleeve 168 is exposed above the surface of the liquid solution so that during the remainder of the purge phase most of the purging air or other gas will be diverted out of the tube string through filter stop sleeve 168 above the surface of the solution in sample chamber 10b so as to avoid further bubbling in the solution even proximate the surface thereof.

At the end of the purge mode when pressure is relieved from sample access tube 14b, and even before initiation of the vacuum fill mode, the liquid level will rise in tube 178 seeking the general surface level in chamber 10b, and negative buoyancy will again be present so as to drop the tube 170 and filter stop sleeve 168 back down to the fully immersed position shown in FIG. 5 so that upon initiation of the vacuum fill mode no air will initially be drawn into the tube string through filter stop sleeve 168.

Sample access tube 14b is flexible, typically being a thin Teflon tube, so that it will not inhibit the up and down movements of sleeve 168 and rigid tube 170.

FIG. 6 illustrates a presently preferred mixing chamber 112 for use in the systems illustrated in FIGS. 2 and 3. The mixing chamber is defined within a generally vertically oriented mixing tube 180 preferably made of glass having an elongated cylindrical upper portion 182 and a downwardly and inwardly tapering frusto-conical lower portion 184. The mixing tube 180 is supported between generally horizontal, parallel top and bottom plates 186 and 188, respectively which may be made of Teflon or other suitable plastic material. Teflon is presently preferred because it is an approved material for the handling of pharmaceuticals. The upper and lower annular ends of mixing tube 180 are seated in respective annular grooves in plates 186 and 188, with respective O-ring seals 190 and 192 in the grooves at the upper and lower ends of tube 180. The assembly is clamped together vertically by a series of peripheral studs or bolts 194.

A tubular delivery spout 196 preferably made of glass is centrally located within mixing tube 180, projecting downwardly into tube 180 from the top plate 186, delivery spout 196 being in fluid communication with the mixing chamber feed conduit 118 as disclosed in FIGS. 2 and 3. The lower end of mixing tube 180 at the apex of the frusto-conical portion 184 thereof is in communication through bottom plate 188 with mixing chamber outlet conduit 120 as also disclosed in FIGS. 2 and 3. As discussed in detail in connection with FIG. 2, measured quantities of sample solution and either diluent or reagent are moved during the sixth or "purge" phase of an operational sequence through the mixing chamber feed conduit 118 and delivery spout 196 into the mixing tube 180, at which time they swirl upwardly and mix together within the mixing tube 180. Then, during the very next phase of operation which is phase one of the following operational sequence, air is introduced under pressure from outlet conduit 120 up into the bottom of mixing tube 180 so as to bubble up into the mixture and cause additional mixing thereof.

FIG. 7 illustrates alternative apparatus for defining and introducing an accurately measured quantity of diluent or reagent which may be utilized in place of the diluent/reagent measure loop 110 of FIG. 2 and 3. The alternative diluent/reagent measuring apparatus of FIG. 7 is generally designated 200 and will be referred to hereinafter simply as measure stop assembly 200. The filter stop membrane forming a part of each of the filter stop devices 38 in FIG. 1 and 94 and 98 in FIGS. 2 and 3 has the characteristic that it requires a polar solvent. Water (HOH) is such polar solvent because of its dominant OH content. An example of a non-polar solvent is benzine. A solution of water and alcohol up to 50% by volume of alcohol remains sufficiently polarized for satisfactory operation of the filter stop membrane, whereas a water-alcohol solution having substantially greater than 50% by volume of alcohol content begins to wet the filter stop membrane causing the membrane to commence leaking moisture. For the purpose of the present application, a polar solvent may be defined as any solvent that is less polarized than a 50% by volume solution of water and alcohol.

Fortunately, most pharmaceuticals may be dissolved in water, and the diluent liquid or reagent liquid employed in the systems of FIGS. 2 and 3 consist principally of water and are sufficiently polarized for use of the preferred filter stop devices of the present invention. However, in the event a nonpolar solvent must be used in the diluent or reagent liquid, then the alternative measure stop assembly 200 may be employed in place of the diluent/reagent measure loop 110 of FIGS. 2 and 3 for providing an accurately measured quantity of diluent or reagent for mixing with the measured quantity of sample solution.

Measure stop assembly 200 includes a generally cylindrical body 202 closed at its ends by upper and lower heads 204 and 206 to define a relatively large, upright overflow chamber 208. Located within overflow chamber 208 is a measuring tube 210 extending generally vertically upwardly from lower head 206, the measuring tube 210 having an open upper end that will overflow into the overflow chamber 208 when measuring tube 210 becomes filled with a measured quantity of liquid.

Measure stop assembly 200 is placed in the system of FIG. 2 in the same position as the diluent/reagent measure loop 110, the measure stop assembly 200 having a fill conduit 214 that provides communication between control valve 86 port *a* and the bottom of measuring tube 210 through lower head 206, and the top of overflow chamber 208 communicating through upper head 204 to part or all of the measure loop conduit 110 which in turn connects to manifold 92 port *c*. The diluent/reagent supply chamber 106 communicates with control valve 86 port *f* through supply conduit 108 as in FIG. 2, while an overflow exhaust conduit 216 provides communication between the bottom of overflow chamber 208 through lower head 206 back to the diluent/reagent supply chamber 106.

The normal operational sequence of the system of FIG. 2 may be employed with measure stop assembly 200 utilized to provide the measured quantity of diluent or reagent. Thus, in the second or "fill" phase of the operational sequence with control valve 86 in the solid line position of FIGS. 2 and 7 and vacuum applied to the conduit 110 from manifold 92 port *c*, diluent or reagent will be drawn from the diluent/reagent supply chamber 106 through supply conduit 108, control valve 86 ports *f* and *a*, through fill conduit 214 into measuring tube 210, the second or fill phase being applied for a sufficient duration of time so that measuring tube 210 will fill with the diluent or reagent and overflow some of the diluent or reagent into the overflow chamber 208 so that measuring tube 210 will be solidly filled with the measured quantity of diluent or reagent. Then, during the sixth or "purge" phase of the operational sequence, with control valve 86 in its dotted line purge position and purge air pressure applied to conduit 110 from manifold 92 port *c*, the measured quantity of diluent or reagent, which is the quantity thereof contained within measuring tube 210 and fill conduit 214 is forced by pressurization in overflow chamber 208 back out from measuring tube 210 and fill conduit 214, through control valve 86 ports *a* and *b*, and diluent/reagent feed conduit 116, and thence through control valve 84 ports *d* and *c* with the measured quantity of sample solution through sample measure loop 102 and control valve 84 ports *f* and *e* and through mixing chamber feed conduit 118 into the mixing chamber 112. At the same time, the excess of diluent or reagent which overflowed from measuring tube 210 during the fill phase is flowed downwardly out of overflow chamber 208 through overflow exhaust conduit 216 back into the diluent/reagent supply chamber 106.

With overflow exhaust conduit 216 unchecked as illustrated in FIG. 7, it will be understood that during the fill or vacuum phase, some diluent or reagent will be drawn directly from the supply chamber 106 through conduit 216 into overflow chamber 208, but this does not interfere with operation of the system, and such diluent or reagent is simply returned back through conduit 216 into supply chamber 106 during the purge or pressure phase. If desired, a downwardly directed check valve may be employed in association with overflow exhaust conduit 216 to avoid such additional circulation of diluent or reagent, but the check valve has been found to be unnecessary.

FIG. 8 presents a greatly enlarged cross-sectional illustration of one of the filter stop devices 94 and a presently preferred mounting thereof in manifold 92. In practice, the filter stop device 94 may be disc-shaped and on the order of about ¼ inch to 5/16 inch in diameter. The filter stop disc 94 is clamped between flared end 220 of conduit tube 124 and an annular shoulder 222 in manifold body 150. The filter stop device 94 consists of a thin, forwardly facing microporous Teflon membrane 224 which is the operative part of the filter stop device, and an integral polypropylene nonwoven filter fabric backing 226. An example of a suitable filter stop material is Gore-Tex Teflon membrane filter material manufactured by W. L. Gore & Associates, Inc. of Elkton, Md., which is obtainable in various membrane pore sizes, as for example pore sizes of 0.2 microns, 0.45 microns, 1.0 microns and 3.0 microns. These membranes of different pore sizes have different water entry pressure differentials, and for the present invention it is preferred to employ this Gore-Tex filter stop material having the membrane with a pore size of 1 microns which has a water entry pressure differential across the membrane of approximately 10 psi, while at the same time having an insignificantly low air flow pressure differential therethrough. Thus, as viewed in FIG. 8, for a pressure differential across the filter stop 94 of less than 10 psi applied by partial vacuum in manifold 92 from the right-hand side of filter stop 94, an aqueous polar solution in conduit 124 at the left-hand or forwardly facing side of filter stop 94 will be completely blocked by the microporous membrane 224 of filter stop 94, while nevertheless air or other gas will be permitted to freely flow from left to right through the filter stop device 94. In practice with the use of such one micron pore size membrane 224, it is preferred to employ a partial vacuum in the systems of FIGS. 1, 2 and 3 on the order of about 8 inches of mercury, or about 4 psi (below atmospheric pressure). Such partial vacuum is adequate to produce the desired flow of liquids in the systems, while nevertheless providing a large margin of extra pressure differential against any possibility of liquid flow from the forwardly facing direction through the filter stop material.

On the other hand, the purge pressure that is provided in the systems of FIG. 1, 2 and 3 is preferably much larger, preferably being on the order of about 30 to 35 psig.

Although various tube diameters and lengths may be employed in the systems of FIGS. 1, 2 and 3, typical tubing for the various lines may have an I.D. of about 0.8 mm., and may range up to about three or more feet in length.

Although it is presently preferred to employ a step switch in association with the timer for controlling the sequential phases of each operational sequence, as for example the step switch 20 in the system of FIG. 1 and the step switch 82 in the systems of FIGS. 2 and 3, it is to be understood that each of the various valves as well as the detector and recorder in any of these systems of FIGS. 1, 2 and 3 may alternatively be actuated by impulses of the timer applied directly to actuating devices such as relays associated with the respective valves, and the detector and recorder, through suitable respective time delay circuits as may be required for the proper sequencing of the valves and the detector and recorder.

Although for most purposes air is a satisfactory gas for use in purging the systems of FIGS. 1, 2 and 3, it is to be understood that if the sample being tested is likely to oxidize too rapidly upon exposure to air, then the system, including the pump inlet, may be operated in an inert gas atmosphere, such as nitrogen. An example of this problem would be the testing of an ascorbic acid solution, in which oxidation takes place so rapidly that measurement of the dissolution rate is extremely difficult.

While the invention has been described with reference to the above disclosure relating to the preferred embodiments, it is understood that numerous modifications or alterations may be made by those skilled in the art without departing from the scope and spirit of the invention as set forth in the appended claims.

We claim:

1. A method of analyzing a liquid chemical sample which comprises the steps of:
   (a) drawing a liquid chemical sample from a source thereof through a first fluid flow path into a flow cell of a chemical analyzer by application of partial vacuum to said flow cell through a second fluid flow path,
   (b) analyzing said sample in said flow cell, and
   (c) forcing said sample from said flow cell back through said first flow path to said source by application of gas pressure to said second fluid flow path.

2. The method of claim 1 wherein said analyzing step comprises detecting the chemical concentration of said sample.

3. The method of claim 1 which comprises the further step of purging said flow cell and fluid flow paths of residual sample by continuing said application of gas pressure for an interval of time after said sample has been returned to said source.

4. The method of claim 1 which comprises the further step of drawing a sufficient quantity of said sample from said source to substantially completely fill said flow cell and overflow some of the sample into said second flow path so as to draw bubbles that may have formed in the flow cell out of the flow cell into said second flow path.

5. The method of claim 4 which comprises the additional step of blocking the flow of liquid at a point in said second flow path during said application of partial vacuum so as to protect the source of said partial vacuum from the flow of said sample thereto.

6. The method of claim 5 wherein said blocking step is accomplished by applying microporous filter stop membrane means across said second flow path at said point, said filter stop membrane means having the physical characteristics of substantially blocking the flow of liquid therethrough while allowing the substantially free passage of gas therethrough.

7. The method of claim 1 which comprises the further step of filtering said sample proximate said source.

8. The method of claim 1 wherein said gas is air.

9. The method of claim 1 wherein said steps are automatically timed and sequenced.

10. The method of claim 1 which comprises the further steps of:
    (a) providing communication between said first flow path and a second liquid chemical source after the first sample has been returned to its source,
    (b) drawing a quantity of a second liquid chemical sample from said second sample source through said first flow path into said flow cell by a second application of partial vacuum to said flow cell through said second flow path,
    (c) analyzing said second sample in said flow cell, and
    (d) forcing said second sample from said flow cell back through said first flow path to said second source by application of gas pressure to said second fluid flow path.

11. The method of claim 10 wherein said second source includes means for filtering said second sample as it is drawn from said second source, and comprising the further step applied between steps a) and b) of purging said filtering means by applying gas pressure to said second flow path for a brief interval of time.

12. The method of claim 10 wherein said steps are automatically timed and sequenced.

13. A method of analyzing a liquid chemical sample which comprises the steps of:
    (a) drawing a liquid sample into a fluid flow path by application of partial vacuum to said flow path,
    (b) blocking the flow of liquid at a point in said flow path during said application of partial vacuum so as to protect the source of said partial vacuum from the flow of said sample thereto,
    (c) introducing a portion of said sample into a flow cell of a chemical analyzer, and
    (d) analyzing said sample in said flow cell.

14. The method of claim 13 wherein said blocking step is accomplished by applying microporous filter stop membrane means across said flow path, said filter stop membrane means having the physical characteristics of substantially blocking the flow of liquid therethrough while allowing the substantially free passage of gas therethrough.

15. The method of claim 13 which comprises the further step of forcing at least a portion of said sample back through at least a portion of said flow path to said source by application of gas pressure to at least a portion of said flow path.

16. The method of claim 15 wherein substantially the entire said sample is forced back to said source.

17. The method of claim 15 which comprises the additional step of purging said portion of said flow path of residual sample by continuing said application of gas pressure for an interval of time after said portion of said sample has been returned to said source.

18. The method of claim 17 which comprises the further step of diverting gas from said sample source during said continued application of gas pressure to minimize bubbling in said sample source.

19. The method of claim 18 wherein said diverting is accomplished by passing said diverted gas out of said flow path through filter stop sleeve means defining a portion of said flow path, said filter stop membrane means having the physical characteristics of substantially blocking the flow of liquid therethrough while allowing the substantially free passage of gas therethrough.

20. A method of analyzing a liquid chemical sample which comprises the steps of:
    (a) moving a liquid chemical sample from a source thereof into a first fluid flow path,
    (b) moving a liquid additive from a source thereof into a second fluid flow path,
    (c) measuring a quantity of said sample from said first flow path and a quantity of said additive from said second flow path,
    (d) mixing said measured quantities of sample and additive together,
    (e) introducing at least a portion of said mixture of sample and additive into a flow cell of a chemical analyzer, and
    (f) analyzing said mixture in said flow cell, said measuring of at least one of said liquids being accomplished by blocking off a portion of the respective said flow path containing said quantity of said liquid.

21. The method of claim 20 wherein said blocking is accomplished at least in part by applying microporous filter stop membrane means across the respective said flow path, said filter stop membrane means having the physical characteristics of substantially blocking the flow of liquid therethrough while allowing the substantially free passage of gas therethrough.

22. The method of claim 20 wherein at least one of said liquid moving steps is accomplished by application of partial vacuum to the respective said flow path.

23. The method of claim 22 which comprises the further step of applying microporous filter stop membrane means across said flow path to which partial vacuum is applied to block the flow of the respective said liquid against passage thereof into the source of said partial vacuum, said filter stop membrane means having the physical characteristics of substantially blocking the flow of liquid therethrough while allowing the substantially free passge of gas therethrough.

24. The method of claim 22 wherein both of said liquid moving steps are accomplished by application of partial vacuum to said flow paths.

25. The method of claim 24 which comprises the further step of applying microporous filter stop membrane means across both of said flow paths to blcok the flow of said liquid against passage thereof into the source of said partial vacuum, said filter stop membrane means having the physical characteristics of substantially blocking the flow of liquid therethrough while allowing the substantially free passage of gas therethrough.

26. The method of claim 20 wherein said mixture of sample and additive is introduced into said flow cell by application of partial vacuum to said flow cell.

27. The method of claim 26 which comprises the further step of interposing microporous filter stop means between said flow cell and the source of said partial vacuum to block the flow of said liquid mixture against passage thereof into the source of partial vacuum, said filter stop membrane means having the physical characteristics of substantially blocking the flow of liquid therethrough while allowing the substantially free passage of gas therethrough.

28. A method of analyzing a liquid chemical sample which comprises the steps of:
    (a) moving a liquid chemical sample from a source thereof into a first fluid flow path,
    (b) moving a liquid additive from a source thereof into a second fluid flow path,
    (c) measuring a quantity of said sample from said first flow path and a quantity of said additive from said second flow path,
    (d) mixing said measured quantites of sample and additive together,
    (e) introducing at least a portion of said mixture of sample and additive into a flow cell of a chemical analyzer, and
    (f) analyzing said mixture in said flow cell, said measuring of at least one of said liquids being accomplished by filling a measuring receptacle in communication with the respective said flow path to overflowing with the respective said liquid.

29. The method of claim 28 wherein said steps are automatically timed and sequenced.

30. The method of analyzing a plurality of liquid chemical samples which comprises the steps of:
    (a) moving a first liquid chemical sample from a source thereof into a first fluid flow path,
    (b) moving liquid additive from a source thereof into a second flow path,
    (c) measuring a quantity of said first sample from said first flow path and a quantity of said additive from said second flow path,
    (d) mixing said measured quantities to produce a first mixture,
    (e) purging said flow paths of said first sample and said additive in preparation for respectively receiving a second liquid sample from a source thereof and further liquid additive from a source thereof,
    (f) introducing at least a portion of said first mixture into a flow cell of a chemical analyzer
    (g) moving said second sample from said source thereof into said first flow path,
    (h) moving said further additive from said source thereof into said second flow path,
    (i) measuring a quantity of said second sample from said first flow path and a quantity of said further additive from said second flow path, and
    (j) analyzing said first mixture in said flow cell.

31. The method of claim 30 which comprises the further steps of:
    (a) mixing said measured quantities of second sample and further additive to produce a second mixture,
    (b) purging said flow cell of said first mixture in preparation for receiving said second mixture,
    (c) purging said flow paths of said second sample and further additive in preparation for respectively receiving a third liquid chemical sample from a source thereof and additional liquid additive from a source thereof,
    (d) introducing at least a portion of said second mixture into said flow cell and
    (e) analyzing said second mixture in said flow cell.

32. The method of claim 30 wherein said measuring of said additive is acomplished at least in part by applying microporous filter stop membrane means across the respective said flow path, said filter stop membrane means having the physical characteristicsof substantially blocking the flow of liquid therethrough while allowing the substantially free passage of gas therethrough.

33. The method of claim 30 wherein said liquid additive is a diluent.

34. The method of claim 30 wherein said liquid additive is a reagent.

35. The method of claim 30 wherein said liquid moving steps are accomplished by applying partial vacuum to the respective said flow paths.

36. The method of claim 35 which comprises the further step of applying microporous filter stop membrane means across both of said flow paths to block the flow of said liquids against passage thereof into the source of said partial vacuum, said filter stop membrane means having the physical characteristics of substantially blocking the flow of liquid therethrough while allowing the substantially free passage of gas therethrough.

37. The method of claim 30 wherein said introducing step is accomplished by application of partial vacuum to said flow cell.

38. The method of claim 37 which comprises the further step of interposing microporous filter stop means between said flow cell and the source of said partial vacuum to block the flow of said first liquid mixture against passage thereof into the source of partial vacuum, said filter stop membrane means having the physical characteristics of substantially blocking the flow of liquid therethrough while allowing the substantially free passage of gas therethrough.

39. The method of claim 37 which comprises the further step of overflowing said flow cell during said introducing step to remove bubbles from said flow cell.

40. The method of claim 30 wherein said steps are automatically time and sequenced.

41. A system for analyzing a liquid chemical sample which comprises:
(a) a source of liquid chemical sample,
(b) chemical analyzing means having a flow cell,
(c) gas pressure/vacuum source means,
(d) first fluid conduit means between said sample source and said flow cell,
(e) second fluid conduit means between said flow cell and said pressure/vacuum source means, and
(f) means for sequentially shifting said pressure/vacuum source means between a vacuum mode wherein said pressure/vacuum source means applies partial vacuum to said second conduit means to draw said sample through said first conduit means into said flow cell for analysis, and a pressure mode wherein said pressure/vacuum source means applies pressure to said second conduit means to return said sample to its said source and purge said flow cell and conduits of said sample.

42. The system of claim 41 wherein said chemical analyzing means comprises a chemical concentration detector.

43. The system of claim 41 wherein said pressure/vacuum source means comprises a gas pump having a pressure outlet and a vacuum inlet, and said shifting means comprises valve means connected to said pump outlet and inlet and to said second conduit means.

44. The system of claim 41 which further comprises:
(a) a plurality of said sources of liquid chemical samples,
(b) sample selector valve means sequentially connectable between each of said sample sources and said first conduit means.

45. The system of claim 44 which comprises timer means connected to said sample selector valve means, to said shifting means and to said analyzing means for automatically shifting said selector valve means from one of said sample sources to another, shifting said pressure/vacuum source between its said vacuum and pressure modes and energizing said analyzing means.

46. The system of claim 41 which comprises microporous filter stop membrane means disposed across said second conduit means for blocking the flow of said sample liquid to said pressure/vacuum source when the latter is in said vacuum mode, said filter stop membrane means having the physical characteristics of substantially blocking the flow of liquid therethrough while allowing the substantially free passage of gas therethrough.

47. The system of claim 41 which comprises microporous filter stop membrane means forming a portion of said first conduit means proximate said sample source to divert gas from said sample source when said pressure/vacuum source is in its said pressure mode and thereby minimize bubbling in said sample source, said filter stop membrane means having the physical characteristics of substantially blocking the flow of liquid therethrough while allowing the substantially free passage of gas therethrough.

48. The system of claim 47 wherein sample filter means is disposed in said first conduit means between said filter stop membrane means and said sample source.

49. The system of claim 48 wherein said first conduit means includes buoyancy section between said sample filter means and said filter stop membrane means, said sample filter means, buoyancy section and filter stop membrane means normally having negative buoyancy and being immersed in said liquid sample below the surface thereof, gas from said pressure/vacuum source entering said buoyancy section during said pressure mode causing said filter means, buoyancy section and filter stop membrane means to have positive buoyance so as to raise said filter stop membrane means above the surface of the sample liquid.

50. A system for analyzing a liquid chemical sample which comprises:
(a) chemical analyzing means having a flow cell,
(b) a source of liquid chemical sample connected to said flow cell,
(c) vacuum source means connected to said flow cell and adapted to selectively draw said sample from said sample source into said flow cell, and
(d) microporous filter stop membrane means between said flow cell and said vacuum source means for blocking the flow of said sample liquid to said vacuum source, said filter stop membrane means having the physical characteristics of substantially blocking the flow of liquid therethrough while allowing the substantially free passage of gas therethrough.

51. A system as defined in claim 50 which is adapted for chemical dissolution rate testing wherein:
(a) said chemical analyzing means comprises a sample concentration detector, and
(b) said sample source comprises a sample dissolution chamber wherein a solid chemical sample is dissolved in a liquid solvent.

52. A system as defined in claim 50 which is adapted for chemical dissolution rate testing wherein:
(a) said chemical analyzing means comprises a sample concentraton detector, and (b) said sample source comprises a source of a mixture of sample and diluent, said diluent being adapted to weaken the concentration of the sample so as to bring the sample within the concentration range of said detector.

53. A system as defined in claim 50 which is adapted for chemical dissolution rate testing wherein
(a) said chemical analyzing means comprises a sample concentration detector, and
(b) said sample source comprises a source of a mixture of sample and reagent, said reagent being adapted to strengthen the concentration of the sample so as to bring the sample within the concentration range of said detector.

54. A system for analyzing a series of liquid chemical samples which comprises:
(a) a plurality of liquid chemical sample sources,
(b) sample selector valve means selectively connectable with each of said sample sources,
(c) a liquid additive source
(d) mixing receptacle means adapted to receive measured quantitites of a selected sample and of said additive,
(e) sample measuring means connected to said selector valve means and to said receptacle means,
(f) additive measuring means connected to said additive source and to said receptacle means,
(g) chemical analyzing means having a flow cell connected to said receptacle means, and
(h) liquid transporting means connected to both of said measuring means and to said receptacle means for transporting sample from a selected sample source and additive from said additive source into the respective said measuring means, transporting measured quantitites of the selected sample and additive from the respective said measuring means into said receptacle means to produce a sample-additive mixture in said receptacle means, and transporting said mixture from said receptacle means into said flow cell for analysis.

55. The system of claim 54 which comprises bypass valve means connected to said sample selector valve means, to said flow cell and to said transporting means, said bypass valve means being selectively operable to provide direct communication between said sample selector valve means and said flow cell which bypasses said additive source and additive measuring means.

56. The system of claim 54 wherein said liquid transporting means comprises pressure/vacuum source means.

57. The system of claim 56 wherein said pressure/vacuum source means is selectively shiftable between a pressure mode and a vacuum mode,
said pressure/vacuum source means being in its said vacuum mode for transporting sample from a selected sample source and additive from said additive source into the respective said measuring means,
said pressure/vacuum source means being in its said pressure mode for transporting measured quantities of the selected sample and additive from the respective said measuring means into said receptacle means, and
said pressure/vacuum source means being in its said vacuum mode for transporting said mixture from said receptacle means into said flow cell.

58. The system of claim 57 which comprises bypass valve means connected to said sample selector valve means, to said flow cell and to said transporting means,
said bypass valve means being selectively operable to a bypass position providing direct communication between said sample selector valve means and said flow cell which bypass said additive source and additive measuring means, and to provide direct communication between said pressure/vacuum source means and said flow cell,
with said bypass valve means in its said bypass position, said pressure/vacuum source means in its said vacuum mode applying partial vacuum to said flow cell to draw sample from a selected sample source into said flow cell for analysis, and in its said pressure mode applying pressure to said flow cell to return said selected sample to its said source and purge said flow cell of said selected sample.

59. The system of claim 57 which comprises microporous filter stop membrane means interposed between said pressure/vacuum source means and the remainder of said liquid transporting means for blocking the flow of liquid to said pressure/vacuum source when the latter is in its said vacuum mode.

60. The system of claim 57 wherein said transporting means further comprises control valve means selectively shiftable between first and second positions connected to said sample selector valve means, both of said measuring means, said receptacle means and said flow cell,
said control valve means in its said first position providing communication between said receptacle means and said flow cell, between said sample selector valve means and said sample measuring means, and between said additive source and said additive measuring means, enabling vacuum from said pressure/vacuum source to transport a first mixture of a first sample and additive from said receptacle means to said flow cell, a second sample from said sample selector valve means to said sample measuring means, and further additive from said additive source to said additive measuring means, and
said control valve means in its said second position providing communication between both of said measuring means and said receptacle means, enabling pressure from said pressure/vacuum source to transport said second sample and further additive from the respective said measuring means to said receptacle means to produce a second mixture of sample and additive in said receptacle means.

61. The system of claim 60 wherein said control valve means in its said second position provides communicaton between said flow cell and drain means, enabling pressure from said pressure/vacuum source to transport said first mixture from said flow cell to said drain means.

62. The system of claim 60 wherein said control valve means in its said second position provides communication between said pressure/vacuum source means and said sample selector valve means, enabling gas pressure from said pressure vacuum source means to purge said source of said second sample.

63. The system of claim 62 wherein the connection between said sample selector valve and at least one of said sample sources comprises conduit means with microporous filter stop membrane means forming a portion thereof proximate said sample source to divert gas from said sample source when said pressure/vacuum source means is in its said pressure mode and thereby minimize bubbling in said sample source, said filter stop membrane means having the physical characteristics of substantially blocking the flow of liquid therethrough while allowing the substantially free passage of gas therethrough.

64. The system of claim 63 wherein sample filter means is disposed in said conduit means between said filter stop membrane means and said sample source.

65. The system of claim 60 which comprises timer means connected to said sample selector valve means, to said pressure/vacuum source means, to said control valve means and to said analyzing means, for shifting said selector valve means from one of said sample sources to another, shifting said pressure/vacuum source means between its said vacuum and pressure modes, shifting said control valve means between its said first and second positions and energizing said analyzing means.

66. The system of claim 57 wherein at least one of said measuring means is defined at least in part by microporous filter stop membrane means, said filter stop membrane means having the physical characteristics of substantially blocking the flow of liquid therethrough while allowing the substantially free passage of gas therethrough.

67. The system of claim 66 wherein said one of said measuring means is said additive measuring means.

68. The system of claim 57 wherein at least one of said measuring means comprises overflow measuring receptacle means.

* * * * *